(12) United States Patent
Polak

(10) Patent No.: US 10,881,855 B2
(45) Date of Patent: *Jan. 5, 2021

(54) FAST FITTING FOR COCHLEAR IMPLANTS

(71) Applicant: MED-EL Elektromedizinische Geraete GmbH, Innsbruck (AT)

(72) Inventor: Marek Polak, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 16 days.

This patent is subject to a terminal disclaimer.

(21) Appl. No.: 16/445,377

(22) Filed: Jun. 19, 2019

(65) Prior Publication Data

US 2019/0299001 A1    Oct. 3, 2019

Related U.S. Application Data

(63) Continuation of application No. 14/316,952, filed on Jun. 27, 2014, now Pat. No. 10,413,726.

(60) Provisional application No. 61/840,523, filed on Jun. 28, 2013.

(51) Int. Cl.
*A61N 1/36*    (2006.01)
*A61N 1/05*    (2006.01)

(52) U.S. Cl.
CPC ..... *A61N 1/36036* (2017.08); *A61N 1/36039* (2017.08); *A61N 1/0541* (2013.01)

(58) Field of Classification Search
CPC ............ A61N 1/36036; A61N 1/36039; A61N 1/0541
See application file for complete search history.

(56) References Cited

U.S. PATENT DOCUMENTS

| 7,801,617 | B2 | 9/2010 | Dijk et al. |
| 10,413,726 | B2 * | 9/2019 | Polak ................. A61N 1/36036 |
| 2013/0079845 | A1 | 3/2013 | Nopp et al. |
| 2013/0138180 | A1 | 5/2013 | Kals et al. |

OTHER PUBLICATIONS

International Searching Authority, Authorized Officer Blaine R. Copenheaver, International Search Report and Written Opinion—PCT/US2014/044491, dated Nov. 4, 2014, 13 pages.

* cited by examiner

*Primary Examiner* — Catherine M Voorhees
*Assistant Examiner* — Roland Dinga
(74) *Attorney, Agent, or Firm* — Sunstein LLP

(57) ABSTRACT

Approaches are described for fitting an implanted cochlear implant having electrode array contacts to an implanted patient. For multiple different fitting methods, each fitting method is assigned one or more electrode contacts wherein no electrode contact is assigned more than one fitting method. For each fitting method, the assigned electrode contacts are fitted according to the fitting method and fitting values for non-assigned electrode contacts are interpolated. Then a fitting is performed for each electrode contact in the electrode array based on a weighted averaging of the fittings for the various different fitting methods.

24 Claims, 4 Drawing Sheets

FAST FITTING FOR COCHLEAR IMPLANTS

This application is a continuation of co-pending U.S. patent application Ser. No. 14/316,952, filed Jun. 27, 2014, which claims priority from U.S. Provisional Patent Application 61/840,523, filed Jun. 28, 2013, both of which are incorporated herein by reference in their entireties.

TECHNICAL FIELD

The present invention relates to hearing implants, and more specifically to fit customization in cochlear implant applications.

BACKGROUND ART

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant processor 108. Besides receiving the processed audio information, the implant processor 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

Cochlear implant systems employ stimulation strategies that provide high-rate pulsatile stimuli to electrode contacts in multi-channel electrode arrays. One specific example is the "Continuous Interleaved Sampling (CIS)"-strategy, as described by Wilson et al., *Better Speech Recognition With Cochlear Implants*, Nature, vol. 352:236-238 (1991), which is incorporated herein by reference. For CIS, symmetrical biphasic current pulses are used, which are strictly non-overlapping in time. The rate per channel typically is higher than 800 pulses/sec. Other stimulation strategies may be based on parallel activation of electrode currents. These approaches have proven to be successful in giving high levels of speech recognition.

For an audio prosthesis such as a cochlear implant to work correctly, some patient-specific operating parameters need to be determined in a fit adjustment procedure where the type and number of operating parameters are device dependent and stimulation strategy dependent. Possible patient-specific operating parameters for a cochlear implant include:

$THR_1$ (lower detection threshold of stimulation amplitude) for Electrode Contact 1

$MCL_1$ (most comfortable loudness) for Electrode Contact 1

Phase Duration for Electrode Contact 1
Amplitude for Electrode Contact 1
Pulse Rate for Electrode Contact 1
$THR_2$ for Electrode Contact 2
$MCL_2$ for Electrode Contact 2
Phase Duration for Electrode Contact 2
Amplitude for Electrode Contact 2
Pulse Rate for Electrode Contact 2
. . .
Number of fine structure channels
Compression
Parameters of frequency, e.g. electrode contact mapping
Parameters describing the electrical field distribution, e.g. spatial spread One approach for an objective measurement of MCLs and THLs is based on the measurement of the eCAPs (Electrically Evoked Compound Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, a recording electrode in the scala tympani of the inner ear is used. The overall response of the auditory nerve to an electrical stimulus is measured very close to the position of the nerve excitation by a given electrode contact. This neural response is caused by the super-position of single neural responses at the outside of the axon membranes. The amplitude of the EAP at the measurement position is between $10\mu V$ and $1800$ $\mu V$. Other objective measurement approaches are also known, such as electrically evoked stapedius reflex thresholds (eSRT).

One common method for fit adjustment is to behaviorally find the threshold (THR) and most comfortable loudness (MCL) value for each separate electrode contact. For this, the stimulation charge on a selected electrode channel is usually increased in steps from zero until the THR or MCL level is reached in a subjective procedure (e.g. method of adjustments) or an objective procedure (e.g., eCAP or eSRT). This increase can be either stimulation burst duration or stimulation burst amplitude or a combination thereof. Typically, for this procedure constant amplitude stimulation bursts with 10-1000 msec duration are utilized. See for example, Rätz, *Fitting Guide for First Fitting with MAESTRO 2.0*, MED-EL, Fürstenweg 77a, 6020 Innsbruck, 1.0 Edition, 2007. AW 5420 Rev. 1.0 (English_EU); incorporated herein by reference. Other alternatives/extensions are sometimes used with a reduced set of operating parameters; e.g. as suggested by Smoorenburg, *Cochlear Implant Ear Marks*, University Medical Centre Utrecht, 2006; U.S. Patent Application 20060235332; which are incorporated herein by reference. Typically each electrode channel is fitted separately without using the information from already fitted electrode channels. The stimulation charge on a given electrode contact typically is increased in steps from zero until the MCL (most comfortable loudness) is reached.

Several approaches currently are used to accelerate the fitting process. One approach is to use a flat map, i.e. use the same MCL or THR value on all electrode channels so that only one electrode channel needs to be fitted. But this approach allows no conclusion to be drawn about the perceptive status (high or less sensitive) of fitted electrode channels and consequently the resulting map can be in much too loud or too soft for some electrode channels. Another approach is to increase electrode stimulation charge during fitting on N adjacent electrode contacts simultaneously from zero onwards and thereby so to speak fit N adjacent electrode contacts simultaneously. These and similar approaches do save time, however, they have the disadvantage of not taking into account electrode-specific particularities, like, e.g., a certain electrode channels having a considerably different MCL value from another electrode channels. A third used approach for example is to not start from zero when fitting an electrode channel, but from a certain fixed value. This approach however has the disadvantage of the fixed starting values possibly being too high with respect on MCL on one electrode channel and possibly being much too low with respect to MCL on another electrode channel. In other words, the risk of over-stimulating the patient exists, while there is still potential of more time savings.

SUMMARY

Embodiments of the present invention are directed to fitting an implanted cochlear implant having electrode array contacts to an implanted patient. For multiple different fitting methods, each fitting method is assigned one or more electrode contacts wherein no electrode contact is assigned more than one fitting method. For each fitting method, the assigned electrode contacts are fitted according to the fitting method and fitting values for non-assigned electrode contacts are interpolated. Then a fitting is performed for each electrode contact in the electrode array based on a weighted averaging of the fittings for the various different fitting methods, The one or more electrode contacts assigned to a given fitting method may be non-adjacent to each other. The fitting methods may include a combination of objective and subjective fitting methods. A sequential or parallel stimulation strategy may be used. And the implanted patient may have a bilateral implant arrangement with left- and right-side electrode arrays whereby all the electrode contacts in both electrode arrays are fit.

Embodiments also include a cochlear implant fitting system using a method according to any of the above, and a computer program product implemented in a tangible computer readable storage medium for fitting an implanted electrode of a cochlear implant to an implanted patient that includes program code for performing a method according to any of the above.

DETAILED DESCRIPTION

It is known that a better fitting can be realized by combining multiple different fitting methods. But it can be very time consuming to fit each active electrode contact multiple times. Embodiments of the present invention are directed to arrangements for an improved fitting process that combines multiple different fitting methods without being overly time consuming.

Figure 1:
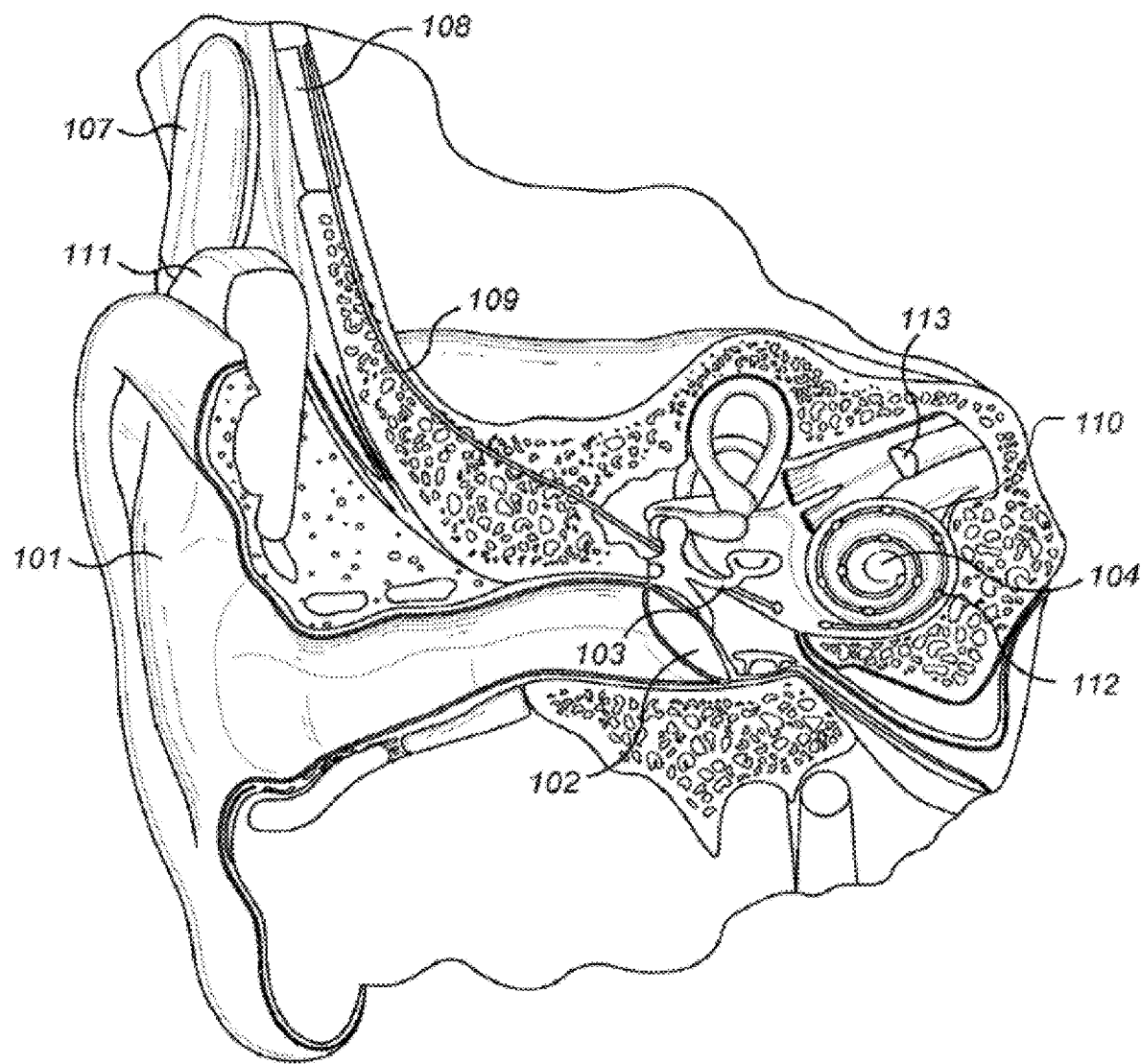
FIG. 1 shows anatomical structures in a human ear having a cochlear implant system.
Figure 2:
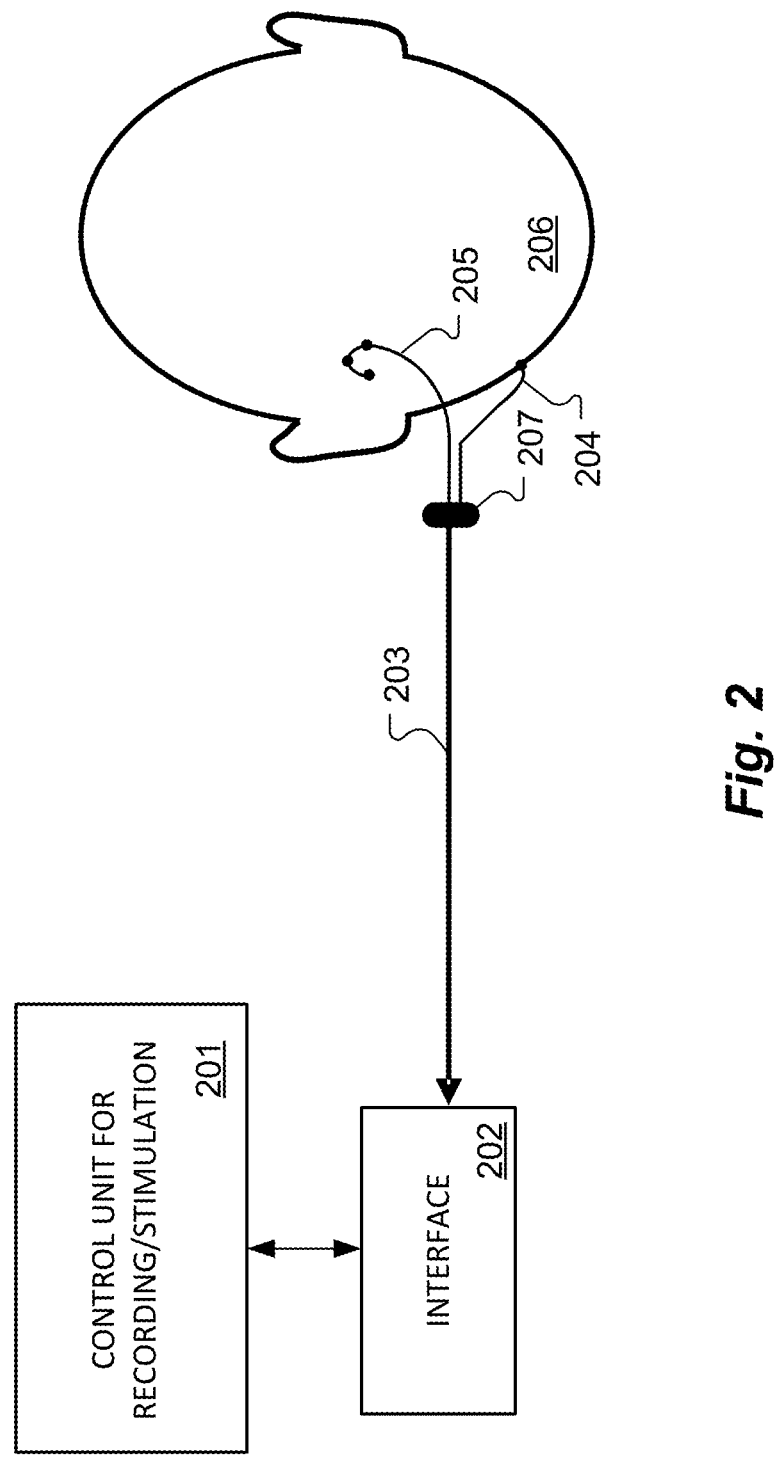
FIG. 2 shows a block diagram of a cochlear implant fitting system according to one specific embodiment of the present invention.
Figure 3:
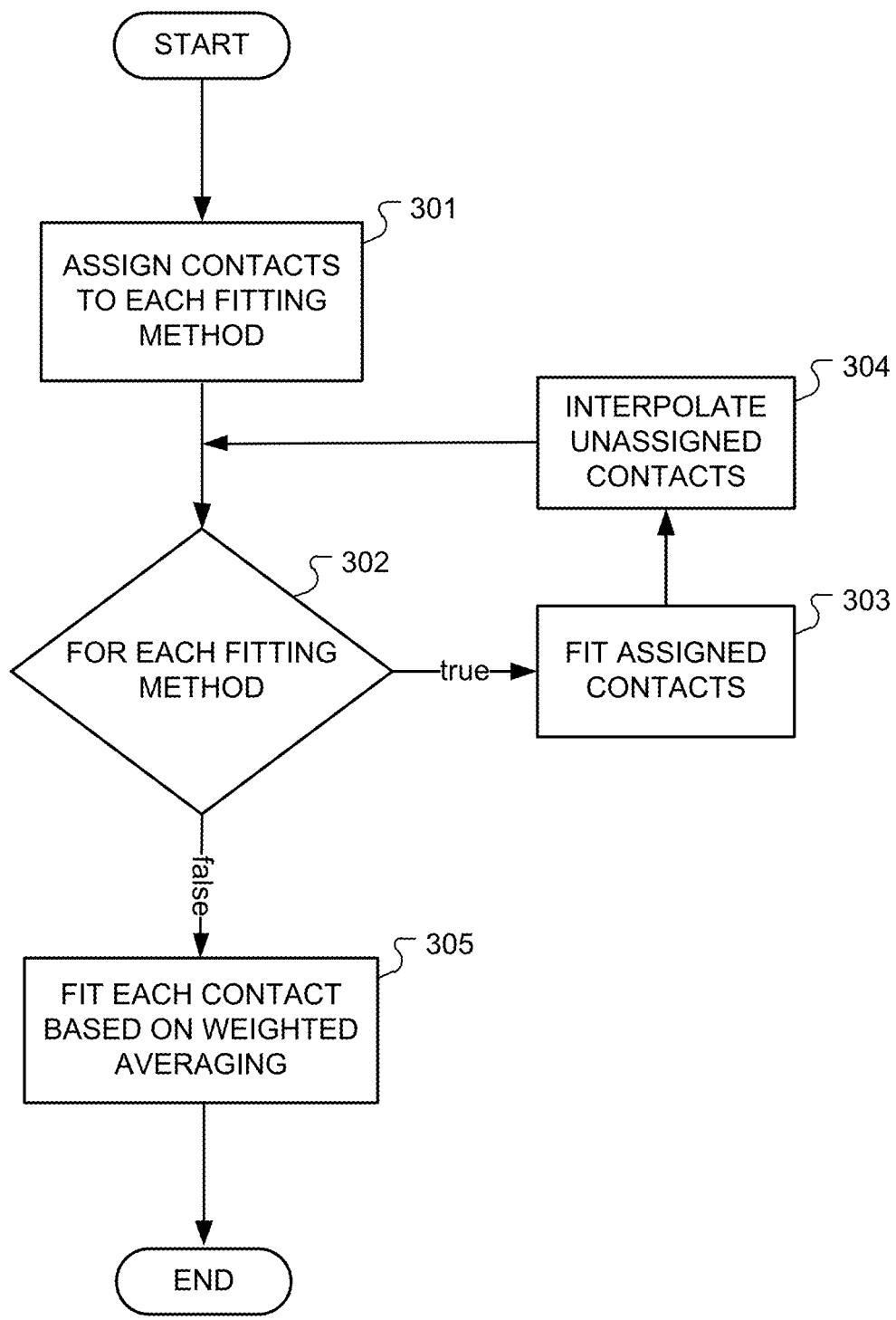
FIG. 3 shows various logical steps in performing an electrode fitting process according to one specific embodiment of the present invention.

FIG. 2 shows a block diagram of a cochlear implant fitting system and FIG. 3 shows various logical steps in performing an electrode fitting process according to one specific embodiment of the present invention. Control Unit 201 for Recording and Stimulation, for example, a Med-El Maestro CI system, generates electrical stimulation signals and analyzes response measurements. Connected to the Control Unit 201 is an Interface Box 202, for example, a Diagnostic Interface System such as the DIB II conventionally used with the Maestro CI system that formats and distributes the input and output signals between the Control Unit 201 and the system components implanted in the Patient 206. For example, as shown in FIG. 2, there may be an Interface Lead 203 connected at one end to the Interface Box 202 and at the other end having Electrode Plug 207 that then divides into a Cochlear Implant Electrode 204 and an Extra-Cochlear Ground Electrode 205. After or during delivering a stimulation pulse, a Cochlear Implant Electrode 204 may be used as a sensing element to determine current and voltage characteristics of the adjacent tissue, for example, for use measuring current spread.

Figure 4:
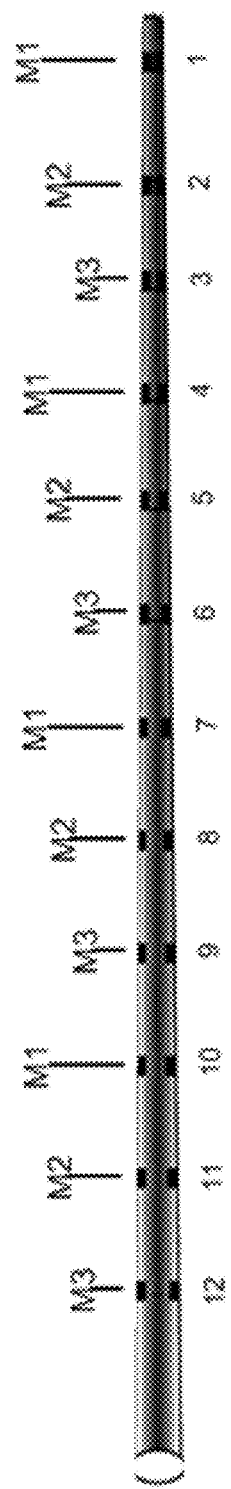
FIG. 4 shows an example of a mapping of fitting methods to electrode contacts according to an embodiment of the present invention.

Using a fitting system such as the one shown in FIG. 2, for multiple different fitting methods, each fitting method is assigned one or more electrode contacts such that each assigned electrode contact is assigned only one fitting method, step 301. For example, FIG. 4 shows an example of a mapping of three different fitting methods M1-M3 to a CI electrode having twelve electrode contacts. For example, fitting method group M1 may be based on behavioral MCL/THR (subjective), fitting method group M2 may be based on eCAP MCL/THR estimation (objective), and fitting method group M3 may be based on stapedius reflex measurement (objective). In the example shown, fitting method M1 is assigned to electrode contacts 1, 4, 7 and 10; fitting method M2 is assigned to electrode contacts 2, 5, 8 and 11; and fitting method M3 is assigned to electrode contacts 3, 6, 9 and 12. The specific electrode contacts each fitting method group should be equidistant and sufficiently separated (non-adjacent).

For each fitting method, step 302, the assigned electrode contacts are fitted according to the fitting method, step 303, and fitting values for non-assigned electrode contacts are interpolated, step 304. The interpolation function can be any suitable function, e.g. linear, non-linear or a fitted-ISO-loudness curve. Using the example shown in FIG. 4:

1. Map M1—electrode contacts 1, 4, 7 and 10, and interpolate the other electrode contacts for M1.
2. Map M2—electrode contacts 2, 5, 8 and 11, and interpolate the other electrode contacts for M2.
3. Map M3—electrode contacts 3, 6, 9 and 12, and interpolate the other electrode contacts for M3.

At this point, for each electrode contact there has been one actual fitting measurement and two interpolations. This yields to a number of fitted curves over the electrodes, each with a different objective measure. A final overall fitting then is performed for each electrode contact in the electrode array based on a weighted averaging of the fittings for the plurality of different fitting methods, step 305:

4. Fit all the electrode contacts based on a weighted averaging of M1, M2 and M3. The weightings may be different for MCL and THR, and also the position of the electrode contact may have an impact:

$$MCL_e = \frac{\sum_{i=1}^{N} w_i MCL_{i,e}}{\sum_{i=1}^{N} w_i}$$

and $$THR_e = \frac{\sum_{i=1}^{N} v_i THR_{i,e}}{\sum_{i=1}^{N} v_i}$$

where
- i—Type of objective or subjective fitting measurement
- e—Electrode contact
- N—number of objective and subjective fitting measurements used
- $MCL_{i,e}$—calculated from measured or interpolated value for electrode contact e and objective or subjective fitting measurement i
- $THR_{i,e}$—calculated from measured or interpolated value for electrode contact e and objective or subjective fitting measurement i
- w—weighting function for MCL
- v—weighting function for THR The different fitting methods should be chosen so that when calculating the final weighted averaging of the fittings, the various systematic measurement errors cancel out as much as possible. The weighted averaging also can take into account the properties of each specific measurement (eCAP, behavioral, stapedius reflex, etc.). That is, each measurement can be classified as an over-estimator or under-estimator of the respective MCL/THR obtained therefrom as shown in Table 1:

| Objective Measurement | Overestimate Correlation Index | Underestimate Correlation Index | Correlation Index |
|---|---|---|---|
| eSRT | 0.9-0.95 | | 0.4-0.6 |
| eCAP | | 0.6-0.7 | 0.5-0.7 |
| eABR | | 0.6 | 0.5-0.7 |
| eMLR | | 0.6-0.7 | 0.5-0.7 |

The different fitting measurement methods should be chosen to cancel out any over- or under-estimates resulting in a more intelligent approach to fitting that is both faster and which results in better final fitting values. To achieve this, the calculated weights per electrode contact may be chosen, for example, to be inverse to the squared standard deviation, i.e. the correlation index of the respective fitting measurement method. In one specific embodiment the weight w, or v, may be calculated by $$w_i = \frac{1}{\sigma_i^2} \text{ or } v_i = \frac{1}{\rho_i^2}$$

Where $\sigma_i$ and $\rho_i$ is the correlation index for the objective or subjective fitting measurement i of MCL and THR respectively. The weights may be positive for over-estimates and negative for under-estimates. The calculated MCL and THR may be adjusted by the over- or under-estimate correlation index and these values may then be used for interpolation. The interpolation may be linear or non-linear, for example a cubic spline. The correlation index $\sigma_i$ and $\rho_i$ may also be interpolated.

The over- and under-estimating should not be linear when the different fitting methods are different in nature; for example, eSRT has a different nature than evoked potentials such as eCAP, eABR and eMLR. Similarly, different specific stimuli are likely to be used in the various different fitting methods. In eSRT, the stimuli used typically varies from 50 msec to 1000 msec and the eSRT thresholds differ up to 2 dB. For eMLR, the stimuli vary from one single pulse to pulse bursts up to about 10 msec, while eABR and eCAP usually use just a single pulse is being used. Underestimate/overestimate for THR may not be as effective as for MCL since the objective methods do not have significantly better correlations—usually they vary from 0.4-0.7—but the correlation is greatly depending on stimulus parameters.

Some previous studies have shown that the best correlations between eSRT and subjectively set MCL are very high (r=0.9-0.95). The electrically evoked compound action potential (eCAP) shows weaker correlations with the MCL (r=0.5-0.7) and THRs (r=0.5-0.7). The correlations of eMLR with subjective levels seem to vary depending on whether the fitting stimuli are single pulses or bursts of multiple stimulus pulses. Preliminary studies have shown that if a burst of stimulus pulses used during the fitting is the same as is used in later CI operation, then the correlation with MCLs is higher. In that case, the stimulation pulse burst usually has identical stimulation rate with identical duration stimulus pulses of at least 1 msec. When a pulse burst is being used the eMLR threshold are lower than when a single pulse is used. And the longer the pulse burst, the lower the eMLR thresholds that are obtained. Despite the fact of high correlation with eSRT, in some individual patients eSRT may fit much less than an eCAP fit, a problem that should be overcome by following embodiments of the present invention. While eSRT is usually equal or louder than subjective MCL, eCAP and eABR thresholds are usually below the MCL with the average of 60% of MCL.

The number of electrode contacts in each of the different fitting method groups may also be varied so that a more reliable measurement may be used on more electrode contacts and a less reliable measurement on fewer electrode contacts. And it might make sense to vary the order of the different fitting methods Mx and/or the order of fitting the electrode contacts within a given fitting method group. In specific embodiments, a sequential or parallel stimulation strategy may be used. And the implanted patient may have a bilateral implant arrangement with left- and right-side electrode arrays whereby the electrode contacts in both electrode arrays are fit.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

For example, a pseudo code representation of a generic embodiment might be set forth as follows:

```
Process FastFitting
    for multiple different fitting methods:
        assign electrode contacts
            *each contact assigned only one fitting method*
        for each fitting method:
            fit assigned electrode contacts
            interpolate non-assigned electrode contacts fitting
                values
        for each electrode contact:
            fit based on weighted averaging of method fittings
```

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant fitting system for fitting an implanted cochlear implant electrode array having a plurality of electrode contacts to an implanted patient, the system comprising:
    means for assigning to each of a plurality of different fitting response measurement methods, one or more electrode contacts, wherein no electrode contact is assigned more than one fitting response measurement method;
    means for each fitting response measurement method to:
        i. use that fitting response measurement method to fit each electrode contact assigned to the fitting response measurement, and
        ii. interpolate fitting values for all of the remaining electrode contacts based on the fitting of the electrode contacts assigned to the fitting response measurement; and
    means for fitting each of the plurality of electrode contacts based on a weighted averaging of the fittings for the plurality of different fitting response measurement methods.

2. A system according to claim 1, wherein the one or more electrode contacts assigned to a given fitting response measurement method are non-adjacent.

3. A system according to claim 1, wherein the fitting response measurement methods include one or more objective fitting response measurement methods.

4. A system according to claim 1, wherein the fitting response measurement methods include one or more subjective fitting response measurement methods.

5. A system according to claim 1, wherein the fitting methods include both objective and subjective fitting response measurement methods.

6. A system according to claim 1, wherein a sequential stimulation strategy is used with the plurality of electrode contacts.

7. A system according to claim 1, wherein a parallel stimulation strategy is used with the plurality of electrode contacts.

8. A system according to claim 1, wherein the implanted patient has a bilateral implant arrangement with left- and right-side electrode arrays whereby all the electrode contacts in both electrode arrays are fit.

9. A computer program product implemented in a tangible computer readable storage medium for fitting an implanted cochlear implant electrode array having a plurality of electrode contacts to an implanted patient, the product comprising:
    program code for assigning to each of a plurality of different fitting response measurement methods, one or more electrode contacts, wherein no electrode contact is assigned more than one fitting response measurement method;
    program code for each fitting response measurement method to:
        i. use that fitting response measurement method to fit each electrode contact assigned to the fitting response measurement, and
        ii. interpolate fitting values for all of the remaining electrode contacts based on the fitting of the electrode contacts assigned to the fitting response measurement; and
    program code for fitting each of the plurality of electrode contacts based on a weighted averaging of the fittings for the plurality of different fitting response measurement methods.

10. A product according to claim 9, wherein the one or more electrode contacts assigned to a given fitting response measurement method are non-adjacent.

11. A product according to claim 9, wherein the fitting response measurement methods include one or more objective fitting response measurement methods.

12. A product according to claim 9, wherein the fitting response measurement methods include one or more subjective fitting response measurement methods.

13. A product according to claim 9, wherein the fitting response measurement methods include both objective and subjective fitting response measurement methods.

14. A product according to claim 9, wherein a sequential stimulation strategy is used with the plurality of electrode contacts.

15. A product according to claim 9, wherein a parallel stimulation strategy is used with the plurality of electrode contacts.

16. A product according to claim 9, wherein the implanted patient has a bilateral implant arrangement with left- and right-side electrode arrays whereby all the electrode contacts in both electrode arrays are fit.

17. A computer based method implemented using at least one hardware implemented processor for fitting an implanted cochlear implant electrode array having a plurality of electrode contacts to an implanted patient, the method comprising:

using the at least one hardware implemented processor to perform the steps of:

assigning to each of a plurality of different fitting response measurement methods, one or more electrode contacts, wherein no electrode contact is assigned more than one fitting response measurement method;

for each fitting response measurement method:

i. using that fitting response measurement method to fit each electrode contact assigned to the fitting response measurement, and ii. interpolating fitting values for all of the remaining electrode contacts based on the fitting of the electrode contacts assigned to the fitting response measurement; and fitting each of the plurality of electrode contacts based on a weighted averaging of the fittings for the plurality of different fitting response measurement methods.

18. A method according to claim 17, wherein the one or more electrode contacts assigned to a given fitting response measurement method are non-adjacent.

19. A method according to claim 17, wherein the fitting response measurement methods include one or more objective fitting methods.

20. A method according to claim 17, wherein the fitting response measurement methods include one or more subjective fitting methods.

21. A method according to claim 17, wherein the fitting response measurement methods include both objective and subjective fitting response measurement methods.

22. A method according to claim 17, wherein a sequential stimulation strategy is used with the plurality of electrode contacts.

23. A method according to claim 17, wherein a parallel stimulation strategy is used with the plurality of electrode contacts.

24. A method according to claim 17, wherein the implanted patient has a bilateral implant arrangement with left- and right-side electrode arrays whereby all the electrode contacts in both electrode arrays are fit.

* * * * *